United States Patent [19]

Niess et al.

[11] 4,248,243
[45] Feb. 3, 1981

[54] SUSPENSION ARM FOR E.K.G. SUCTION ELECTRODES

[75] Inventors: Eduard Niess; Heiner Hoffmann, both of Herrlingen, Fed. Rep. of Germany

[73] Assignee: Fa. Ingeborg Niess Elektromedizinische Apparate, Blaustein-Herrlingen, Fed. Rep. of Germany

[21] Appl. No.: 69,161

[22] Filed: Aug. 23, 1979

[30] Foreign Application Priority Data

Aug. 25, 1978 [DE] Fed. Rep. of Germany ....... 2837279

[51] Int. Cl.³ .............................................. A61N 1/04
[52] U.S. Cl. .................................................... 128/696
[58] Field of Search .............. 128/630, 639, 643, 695, 128/696, 710, 712, 714, 731, 733

[56] References Cited

U.S. PATENT DOCUMENTS

| | | | |
|---|---|---|---|
| 2,439,559 | 4/1948 | Buffington | 128/639 |
| 3,640,270 | 2/1972 | Hoffmann | 128/643 |
| 3,762,398 | 10/1973 | Schefke et al. | 128/630 |
| 4,191,196 | 3/1980 | Bradley et al. | 128/733 |

OTHER PUBLICATIONS

Groom et al., "American Journal of Medical Electronics", Oct.-Dec., 1964, pp. 261–265.

*Primary Examiner*—William E. Kamm
*Attorney, Agent, or Firm*—Karl F. Ross

[57] ABSTRACT

A gas compressor and the electrical circuitry for an EKG or the like are carried in a support having a post whose upward end carries one end of a parallelogrammatic linkage the other end of which is a head from which hang a plurality of suction-type electrodes. One long link of the parallelogrammatic linkage is formed by a pair of metal tubes, one of which conducts compressed air to the electrode-carrying head, so that this compressed air can operate jet pumps in the electrodes to hold same on the patient, and the other tube contains a multiconductor wire connected to the various electrodes. Thus the gas feed is conveniently housed in the supporting linkage and the electrical conductors are all well shielded within the metal tubing.

10 Claims, 3 Drawing Figures

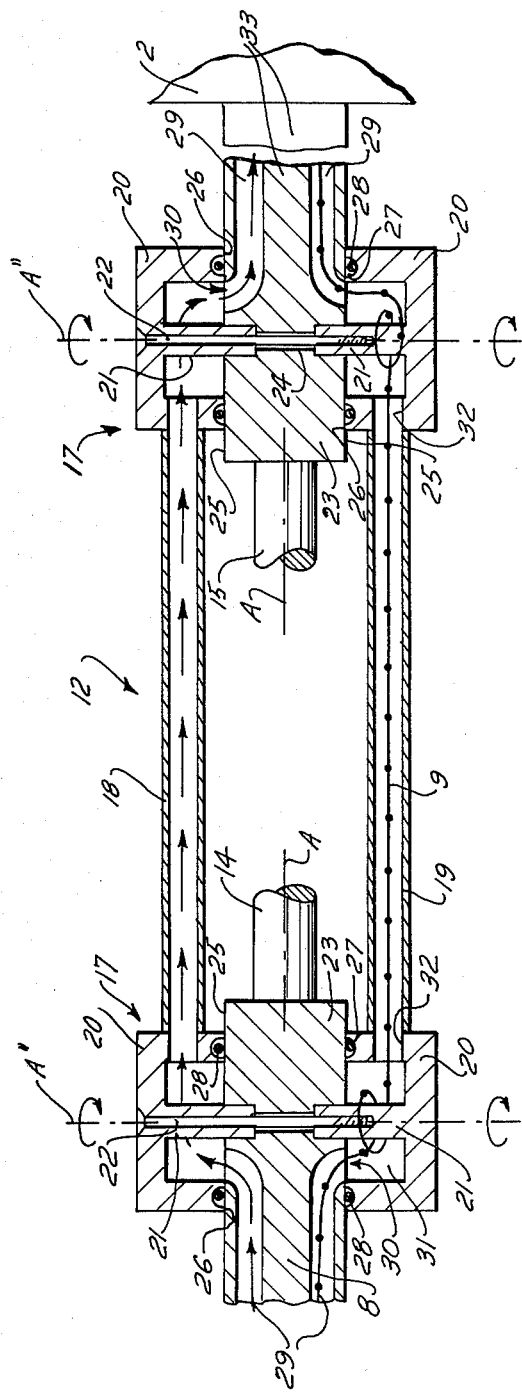

SUSPENSION ARM FOR E.K.G. SUCTION ELECTRODES

FIELD OF THE INVENTION

The present invention relates to a connection assembly for suction electrodes. More particularly this invention concerns an assembly for making the compressed-air and electrical connections to suction electrodes such as used in an electrocardiogram (EKG).

BACKGROUND OF THE INVENTION

A medical electronic diagnostic or test device such as an EKG, electroencephalogram (EEG) or the like normally has a plurality of electrodes which must be positioned on respective locations on the body of the person being monitored. These electrodes form electrical contacts with the respective locations on the body, and allow readings of various functions to be taken.

German Pat. No. 1,939,523 and commonly owned equivalent U.S. Pat. No. 3,640,270 disclose a suction electrode for such an EKG or EEG. The electrode has a feed tube provided with a conductor, and terminating at its free end in a suction cup having a terminal connected to the connector and provided internally with a small jet pump. Normally a conductive jelly is applied to this suction cup, and compressed air is fed through the tube to the respective jet pump to form a low-pressure zone inside the suction cup. This allows the suction cup to be adhered tightly to the body. A compressed-air source and jet pump are used rather than a simple suction pump, as such a suction pump would inherently suck in some of the conductive jelly applied to make a good electrical connection, and eventually this jelly would form a conductive bridge between the various electrodes and the suction pump. The outlets of each of these jet pumps will emit small amounts of the conductive jelly, along with the air creating, via the jet-pump effect, the low-pressure zone that adheres the respective suction cup in place.

It is standard practice simply to plug the tubes into respective sockets on the EKG. These sockets can be set up so as to supply compressed air to the respective feed tubes, while making the electrical connections necessary for the respective electrodes.

Such an arrangement often leaves a tangle of feed tubes and wires that must be painstakingly sorted out each time the apparatus is used. Furthermore the designers of the equipment must constantly trade off lead length for the electrodes with efficiency, as when long pneumatic lines are provided for the electrodes pressure losses are a constant problem, and electrical problems frequently develop when the long electrical leads pick up transient signals from adjacent electronic equipment or magnetic devices. Providing short leads minimizes these problems, but on the other hand makes it necessary to virtually nestle the patient up to the EKG, a situation which makes its operation relatively difficult.

Another disadvantage with these systems, in particular when used in an EKG, is that the equipment employed is relatively bulky and hard to handle. Normally the EKG is used in combination with an oscilloscope that displays whatever process is being monitored. This oscilloscope, and the EKG, have relatively large power supplies whose transformers must be provided with expensive MU-metal shielding. It is therefore normal for this equipment to be mounted on several rolling tables whose transportation to the use location is complex. The relatively heavy equipment on top of light-duty tables becomes very top-heavy, so that extreme care must be exercised in rolling about such equipment.

OBJECTS OF THE INVENTION

It is therefore an object of the present invention to provide an improved electrode-connection assembly for interconnecting suction electrodes with a piece of electromedical equipment containing electrical circuitry to be connected to these electrodes and a source of compressed gas.

Another object is to provide an improved mounting assembly for the suction electrodes of an EKG.

Yet another object is to provide such an arrangement which makes the electromedical equipment easier to use.

SUMMARY OF THE INVENTION

These objects are attained according to the instant invention by hanging the suction electrodes from a head connected via an outrigger-type parallelogrammatic linkage to a support column connected to the electromedical apparatus and to the compressed-gas source. This parallelogrammatic linkage has a pair of short upright links pivotal about and centered on upright axes on the electrode-carrying head and on the support, and having a pair of generally horizontal long links spaced vertically above each other and pivoted at their ends on these short links. One of these long links is formed with a pair of passages one of which acts as a gas conduit extending between the compressed-gas source and the electrodes, and the other of which acts as a shielded guide for a multiconductor cable whose conductors are connected to the electrodes.

More particularly according to this invention the passage-forming long link is formed as a pair of parallel metal tubes provided at their ends with connector pieces or cups that engage flatly against corresponding portions of the respective short links. Each of these pairs of tubes is centered on a respective pivot axis extending through the respective portion of the respective short link, and is formed centered on this axis with an annular axially open recess or groove into which the respective tube opens. Each short link is provided with an axially opening bore that opens into this annular groove in any radial position of the passage-forming long links with respect to this short link. Radially outward from each of these grooves may be another groove provided with an O-ring that not only forms a good fluidtight seal between the respective end part and the short link, but which also provides at least limited braking action against pivoting between these two parts so that the head will remain in the position it is set in once released.

Accordingly to further features of this invention the support includes a base and an upwardly extending post at the top of which is provided one of the short links. This base may contain the main power transformer and the compressor for the apparatus in question, so that extensive shielding is not necessary. What is more providing these relatively weighty items in the bottom of the support makes it extremely stable. Thus it is possible to mount a table or shelf well up on this support for the display oscilloscope, without making the device so top-heavy that it is difficult to move about. In fact, approximately two-thirds of the mass of such an apparatus is normally in these components so that it can be, according to this invention, provided in the base, so that the unit is very stable. What is more, since the conduit extending from the compressor all the way to the electrode-suspending head is formed by completely rigid materials, there is relatively little pressure lost and a smaller compressor than is normally considered necessary may be used.

BRIEF DESCRIPTION OF THE DRAWING

FIG. 2 is a large-scale sectional view of a detail of the connection assembly of FIG. 1; and FIG. 3 is a large-scale view of a detail of FIG. 1.

SPECIFIC DESCRIPTION

Figure 1:
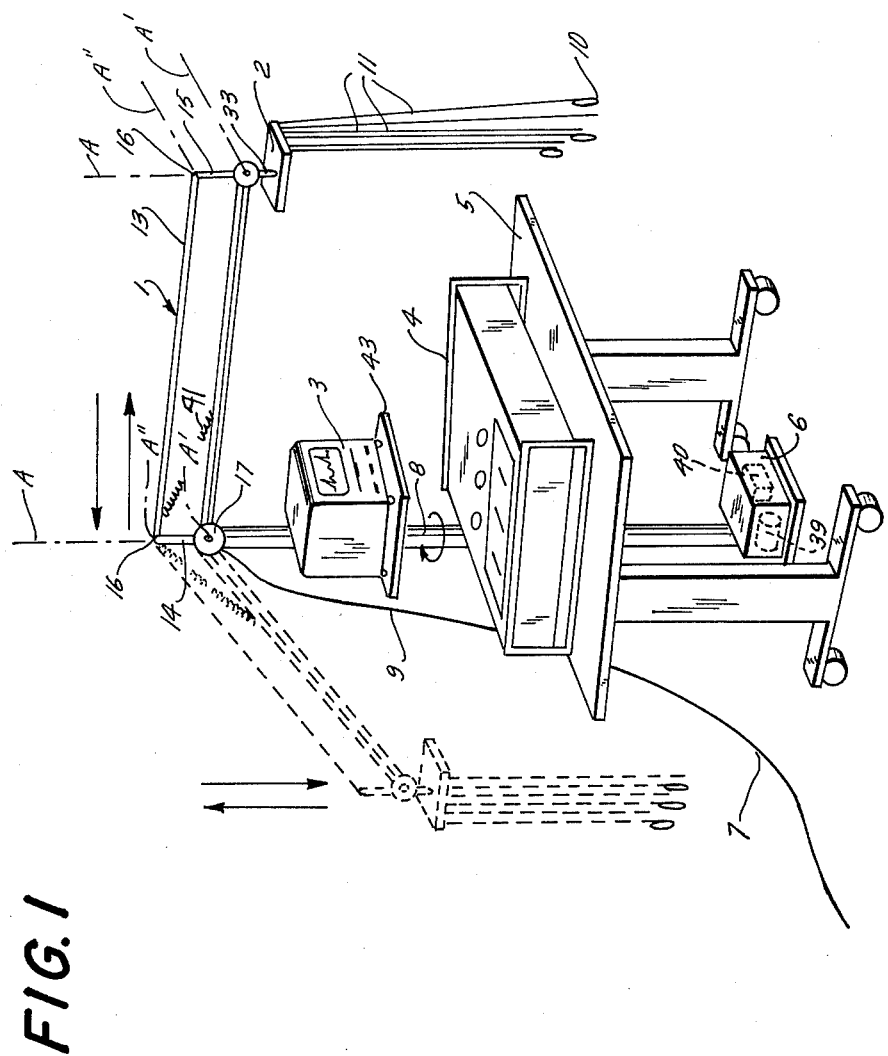
FIG. 1 is a perspective view of the apparatus according to this invention.

The apparatus according to this invention comprises an electrocardiogram 4 having a display oscilloscope 3 and connected via a cord 9 through a parallelgrammatic linkage 1 to a head 2 from which are suspended a plurality of electrotubes 11 having at their ends suction tips 10. The electrocardiogram 4 is carried on a table 5 and is supplied electricity via line cord 7. A support has a base 6 containing a voltage transformer 40 for the electrocardiogram 4 and oscilloscope 3 and a compressor 39. This support further has an upright support pipe or post 8 provided with a shelf 43 on which the oscilloscope 3 is mounted.

The parallelogrammatic linkage comprises a pair of vertically spaced and generally horizontally extending long links 12 and 13 and a pair of upright short links 14 and 15, the latter being centered on upright axis A. The lower link 12, which will be described in greater detail below, is secured at its end at pivots 17 defining axes A' at the lower ends of the short lengths 14 and 15. The upper link 13 is a solid rod and is connected at pin pivots 16 defining horizontal axes A" to the upper ends of the short links 14 and 15. A diagonal tension spring 41 compensates for the downward pull of gravity on the arrangement.

Each of the electrode tips 10 is formed as shown in FIG. 3 as a suction cup connected via the respective feed tube 11 and an electrical wire 34 to the head 2, which in turn is connected by means of a short rod 33 to the lower end of the outer short link 15. This suction-cup tip is provided internally with a jet pump 35 having a low-pressure intake 36 opening into the suction cup, a high-pressure input 37 connected to the tube 11, and a medium-pressure outlet 38. This structure is substantially identical to that described in above-cited German Pat. No. 1,939,523.

As shown in FIG. 2 the lower long link 12 is formed as a pair of parallel identical metal tubes 18 and 19 terminating at cup-shaped end members 20 that each have a central pin 21 lying on the respective axis A". In FIG. 2 the axes A of the short links 14 and 15 are shown to be coaxial for ease of view, whereas in reality these two axes A are always parallel to each other.

The links 14 and 15 have end pieces 23 formed with central-stepped bores 24 receiving the respective pins 21. These pins 21 in turn are provided internally with screws 22 extending along the axes A" and holding a respective pair of end parts 20 in contact with the respective pieces 23. Each of these end parts 20 has a planar face 26 bearing on the corresponding planar face 25 of the piece 23. In addition each of these faces 26 is formed with an annular groove 27 provided with an O-ring 28 bearing axially on the face 25. In effect the end parts 20 form annular chambers 31 concentric to the respective axes A'. The part 23 of the short link 14 is formed with a pair of bores 29 extending longitudinally along the respective axes A and having mouths 30 opening axially of the axes A". Thus in any angular position of the parts 23 relative to the end pieces 20 fluid will be able to flow from the passages 29 into the annular chamber 31. In addition the wall of each of the end parts 20 is formed with a radial bore 32 over which is secured the end of the respective tube 18 or 19.

Thus the compressed air from the compressor 39 can flow up through one of the passages 29 into the chamber 31 at one end of the tube 18, then along this tube 18 and into the chamber 31 at its opposite end, whence it can flow through the passage 29 in the stem 33 to the head 2 where it flows out through the flexible tube 11 to the suction-cup end 10. The other passage formed in part by the metal tube 19 receives the multiconductor cable or wire 9 and can also, if desired, be used for fluid flow.

Thus with the system according to the instant invention compressed air is conducted to the head 2 with virtually no losses in spite of the fact that it passes through two pivots 17. As all of the parts that form the conduit for this compressed air are rigid there will be virtually no losses. Furthermore since the cable 9 is completely shielded by hard metal parts the likelihood of picking up transients or the like is greatly reduced. What is more this cable 9 itself is effectively protected against accidental damage.

The assembly is fully portable, and can easily be rolled to the use location without being likely to tip over, since most of the weight of the device lies in the heavy base 6. What is more the head 2 need merely be swung over a patient being examined so that the ends 11 can be connected to him or her very conveniently.

We claim:

1. In combination with an electromedical apparatus having electrical circuitry and a compressed-air source connectable to a plurality of suction electrodes, an electrode-connection assembly comprising:
   a support defining an upright pivot axis and connected to said apparatus;
   a head defining another upright axis and suspending said suction electrodes;
   respective horizontally spaced head and support short links extending along the respective axes on said head and support;
   a first long link extending generally horizontally between said short links;
   a second long link extending generally horizontally between said short links and generally parallel to and offset vertically from said first link, said second link forming a pair of passages one of which is a compressed-gas passage extending between said source and said head;
   an electrical wire extending in the other of said passages between said circuitry and said electrodes; and
   pivots interconnecting said links as a parallelogrammatic linkage for vertical and horizontal movement of said head with said electrodes relative to said support.

2. The combination defined in claim 1, wherein each of said suction electrodes comprises:
   a suction-cup end;
   a jet pump generally at said end and having a high-pressure input, a low-pressure intake, and a medium-pressure outlet, said intake opening inside said suction-cup end;

a flexible tube interconnecting said high-pressure input to said head and therethrough and through said one passage to said compressed-gas source; and an electrical conductor extending from said end along said tube to said wire and being connected via said wire to said circuitry.

3. The combination defined in claim 2 wherein said passages extend through the pivots at the ends of said second long link.

4. The combination defined in claim 3 wherein said long arm is of metallic shielding material.

5. The combination defined in claim 4 wherein said pivots at said ends of said second long link each comprise a pair of like cups flanking the respective short link, fixed on said second link, pivotal on the respective short link, and each connected to a respective passage.

6. The combination defined in claim 5 wherein each of said cups has a flat face substantially perpendicular to the respective horizontal axis with an annular groove communicating with one of said passages, each of said short links having a pair of flat faces each flatly engaging the flat face of the respective cup, each short link further being formed with a pair of link passages opening at the respective flat faces of said link.

7. The combination defined in claim 6 wherein the flat face of each cup has radially outside of the respective first-mentioned groove a second such groove provided with an O-ring engaging the respective flat face of the respective short link.

8. The combination defined in claim 1 wherein said second link is formed by a pair of metallic tubes each constituting a respective one of said passages.

9. The combination defined in claim 1, further comprising a holder for an oscilloscope on said support.

10. The combination defined in claim 1 wherein said support includes a base including a voltage transformer and a compressor constituting said source and an upright post extending upwardly from said base and having an upper end carrying said respective short link.

* * * * *